US008616149B2

(12) United States Patent
Hosokawa et al.

(10) Patent No.: US 8,616,149 B2
(45) Date of Patent: Dec. 31, 2013

(54) APPARATUS FOR MANUFACTURING A TAMPON

(75) Inventors: Masashi Hosokawa, Kagawa (JP); Mitsuhiro Wada, Kagawa (JP); Satoshi Nozaki, Kagawa (JP)

(73) Assignee: Uni-Charm Corporation, Shikokuchuo-Shi, Ehime (JP)

( * ) Notice: Subject to any disclaimer, the term of this patent is extended or adjusted under 35 U.S.C. 154(b) by 0 days.

(21) Appl. No.: 13/258,021

(22) PCT Filed: Mar. 10, 2010

(86) PCT No.: PCT/JP2010/054037
§ 371 (c)(1),
(2), (4) Date: Dec. 9, 2011

(87) PCT Pub. No.: WO2010/110075
PCT Pub. Date: Sep. 30, 2010

(65) Prior Publication Data
US 2012/0086140 A1    Apr. 12, 2012

(30) Foreign Application Priority Data
Mar. 23, 2009  (JP) .................................. 2009-070649

(51) Int. Cl.
*B05C 1/02*  (2006.01)
(52) U.S. Cl.
USPC ........... 118/206; 118/101; 118/244; 118/304; 118/324; 264/129; 425/94; 427/359; 427/398.2; 427/428.01; 427/428.19
(58) Field of Classification Search
USPC ............ 156/443; 264/37.1, 129; 425/94, 230, 425/238; 427/398.1, 359, 428.01, 428.08, 427/428.19; 118/101, 244, 304, 324
See application file for complete search history.

(56) References Cited

U.S. PATENT DOCUMENTS

| | | | |
|---|---|---|---|
| 3,595,236 A * | 7/1971 | Corrigan et al. | 604/363 |
| 3,736,903 A | 6/1973 | Townsend | |
| 3,821,350 A * | 6/1974 | Suchane | 264/257 |
| 6,180,172 B1 * | 1/2001 | Hasenkamp et al. | 427/277 |
| 6,670,523 B1 | 12/2003 | Mahr et al. | |
| 6,888,043 B2 | 5/2005 | Geiser et al. | |
| 6,979,663 B2 * | 12/2005 | Wolfe et al. | 502/159 |

(Continued)

FOREIGN PATENT DOCUMENTS

DE   2125551 B   7/1972
JP   49-120092 U   10/1974

(Continued)

OTHER PUBLICATIONS

International Search Report for PCT/JP2010/054037 mailed Jun. 15, 2010.

(Continued)

*Primary Examiner* — Alexander Weddle
(74) *Attorney, Agent, or Firm* — Loew Hauptman & Ham, LLP (57) ABSTRACT

A manufacturing method for a tampon having an absorbent body that absorbs liquid includes obtaining the absorbent body by compressing and shaping an absorbent-body material, and applying a melted agent to an outer surface of the absorbent body, the outer surface having a temperature lower than or equal to a freezing point of a main ingredient of the agent.

12 Claims, 8 Drawing Sheets

(56) References Cited

U.S. PATENT DOCUMENTS

| | | |
|---|---|---|
| 2002/0173760 A1 | 11/2002 | Pasquini et al. |
| 2006/0264857 A1* | 11/2006 | Colbert ........................ 604/360 |
| 2008/0065041 A1* | 3/2008 | Stan et al. ................ 604/385.18 |

FOREIGN PATENT DOCUMENTS

| | | |
|---|---|---|
| JP | 49120092 A | 10/1974 |
| JP | 2002-532200 A | 10/2002 |
| JP | 2003-523800 A | 8/2003 |
| JP | 2005-536237 A | 12/2005 |
| JP | 2008504077 A | 2/2008 |
| JP | 2008-200169 A | 9/2008 |

OTHER PUBLICATIONS

Extended European Search Report for 10755875.1, dated Nov. 28, 2012.

Office Action dated May 15, 2013 corresponds to Chinese application No. 201080022244.X.

* cited by examiner

APPARATUS FOR MANUFACTURING A TAMPON

RELATED APPLICATIONS

The present application is a National Phase of International Application Number PCT/JP2010/054037, filed Mar. 10, 2010 and claims priority from, Japanese Application Number 2009-070649, filed Mar. 23, 2009.

TECHNICAL FIELD

The invention relates to a manufacturing method for a tampon, and a manufacturing apparatus for a tampon.

BACKGROUND ART

Tampons including an absorbent body that absorbs liquid such as menstrual blood has been well known. In some of such tampons, an agent is applied onto an outer surface of the absorbent body thereof.

In manufacturing such tampons, a process in which the absorbent body is obtained from the absorbent-body material and a process in which the agent is applied such that the agent adheres to the outer surface of the absorbent body are needed.

CITATION LIST

Patent Literature

[PTL 1] Japanese Unexamined Patent Application Publication (Translation of PCT Application) No. 2005-536237

SUMMARY OF THE INVENTION

Technical Problem

There was a possibility that the agent does not properly take effect when inserting into the vaginal cavity a tampon manufactured by a manufacturing method including the foregoing process. Therefore, a manufacturing method for a tampon having an agent that properly takes effect has been demanded.

This invention has been made in view of the above problems, and an advantage thereof is to provide a manufacturing method etc for a tampon having an agent that properly takes effect while the tampon being within the vaginal cavity.

Solution to Problem

An aspect of the invention to achieve the above advantage is a manufacturing method for a tampon having an absorbent body that absorbs liquid, including:
  obtaining the absorbent body by compressing and shaping an absorbent-body material; and
  applying a melted agent to an outer surface of the absorbent body, the outer surface having a temperature lower than or equal to a freezing point of a main ingredient of the agent.

Other features of this invention will become apparent from the description in this specification and the attached drawings.

Effects of the Invention

According to the invention, is achieved a manufacturing method etc for a tampon having an agent that properly takes effect while the tampon being within the vaginal cavity.

MODE FOR CARRYING OUT THE INVENTION

At least the following matters will be made clear by the description in the present specification and the accompanying drawings.

A manufacturing method for a tampon having an absorbent body that absorbs liquid, including:
  obtaining the absorbent body by compressing and shaping an absorbent-body material; and
  applying a melted agent to an outer surface of the absorbent body, the outer surface having a temperature lower than or equal to a freezing point of a main ingredient of the agent.

In such a case, a manufacturing method for a tampon having an agent that properly takes effect while the tampon being within the vaginal cavity is achieved.

In such a manufacturing method, desirably,
  the method further includes
    bringing a cooling medium into contact with the agent applied to the outer surface, the cooling medium being cooled to a temperature lower than or equal to the freezing point.

In such a case, a manufacturing method for a tampon having an agent that more properly takes effect while the tampon being within the vaginal cavity is achieved.

In such a manufacturing method, desirably,
  the method further includes
    fixing a shape of the absorbent body by heating the absorbent body that is obtained by compressing and shaping the absorbent-body material, and
    cooling the absorbent body whose shape is fixed such that an outer surface of the absorbent body has a temperature lower than or equal to the freezing point, and in applying the agent, the melted agent is applied to the outer surface of the absorbent body, the outer surface being cooled to the temperature lower than or equal to the freezing point.

This makes it possible to shorten the manufacturing process.

A manufacturing apparatus for a tampon having an absorbent body that absorbs liquid, including:
- a compressing-shaping unit with which the absorbent body is obtained by compressing and shaping an absorbent-body material; and
- an applying unit that applies a melted agent to an outer surface of the absorbent body, the outer surface having a temperature lower than or equal to a freezing point of a main ingredient of the agent.

In such a case, a manufacturing apparatus for a tampon having an agent that properly takes effect while the tampon being within the vaginal cavity is achieved.

In such a manufacturing apparatus, desirably, the apparatus further includes
- a cooling-medium-contact unit that brings a cooling medium into contact with the agent applied by the applying unit to the outer surface, the cooling medium being cooled to a temperature lower than or equal to the freezing point.

In such a case, a manufacturing apparatus for a tampon having an agent that more properly takes effect while the tampon being within the vaginal cavity is achieved.

In such a manufacturing apparatus, desirably, the apparatus further includes
- a heating unit that fixes a shape of the absorbent body by heating the absorbent body that is obtained by compressing and shaping the absorbent-body material with the compressing-shaping unit; and
- a cooling unit that cools the absorbent body whose shape is fixed by the heating unit such that the outer surface has a temperature lower than or equal to the freezing point,
- the applying unit that applies the melted agent to the cooled outer surface of the absorbent body by the cooling unit to the temperature lower than or equal to the freezing point.

This makes it possible to shorten the manufacturing process.

In such a manufacturing apparatus, desirably, the apparatus further includes
- a cooling-medium-contact unit that brings a cooling medium into contact with the agent applied by the applying unit to the outer surface, the cooling medium being cooled to a temperature lower than or equal to the freezing point,
- the applying unit applies the melted agent to the outer surface of the absorbent body that is conveyed by the cooled conveyor belt, and
- both of the cooling unit and the cooling medium are the conveyor belt.

In such a case, an effective manufacturing apparatus is achieved.

In such a manufacturing apparatus, desirably, the cooling-medium-contact unit is a cool-air-blowing unit that blows onto the agent cool air as a cooling medium.

This makes it possible to cool the agent easily.

In such a manufacturing apparatus, desirably, the applying unit includes
- a transferring belt that transfers and applies the melted agent to the outer surface of the absorbent body with being in contact with the outer surface, and
- a supplying unit that supplies the melted agent to the transferring belt.

This can make the manufacturing process simpler.

In such a manufacturing apparatus, desirably, the applying unit includes
- a moving unit that moves a frozen-agent-adhering sheet having the frozen agent that adheres to a one surface of the sheet, with the one surface being in contact with the outer surface of the absorbent body, and
- a heating-transferring unit that melts the frozen agent and transfers the melted agent to the outer surface by keeping in contact with another surface of the frozen-agent-adhering sheet and heating the frozen-agent-adhering sheet.

This makes it possible to configure a manufacturing apparatus that is difficult to be soiled with the agent.

Configuration of Tampon

Firstly, the configuration of a tampon 10 will be described with reference to FIGS. 1 to 5.

Figure 1:
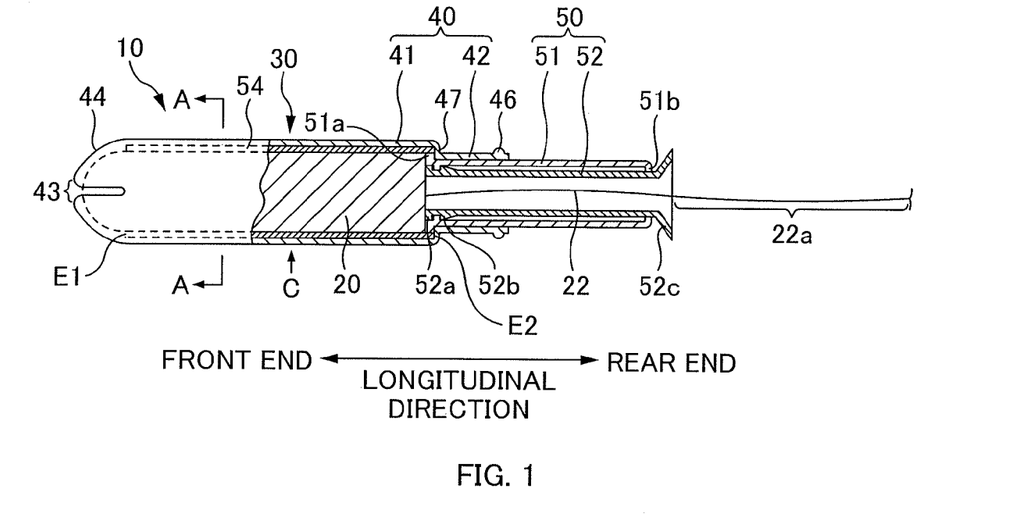
FIG. 1 is a cross-sectional view showing components of a tampon 10.
Figure 2:
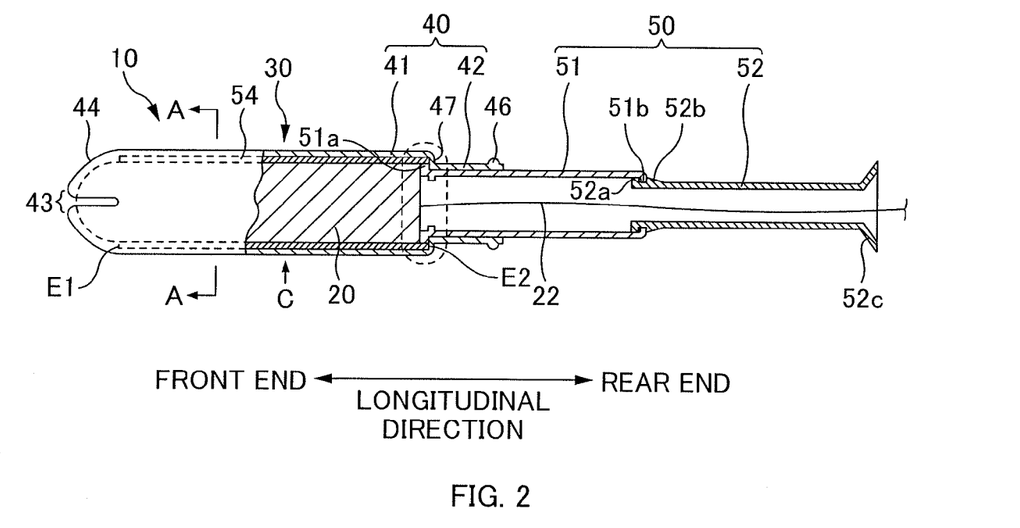
FIG. 2 is a cross-sectional view showing components of the tampon 10.
Figure 3:
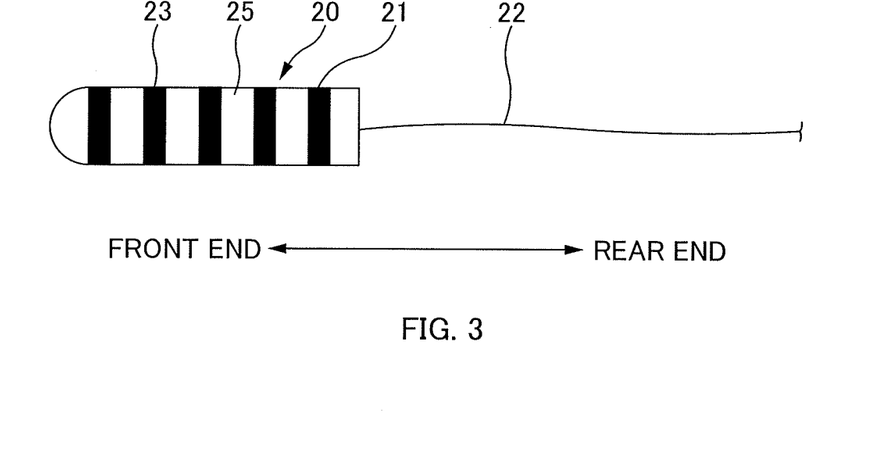
FIG. 3 is an external view of a tampon body 20.
Figure 4:
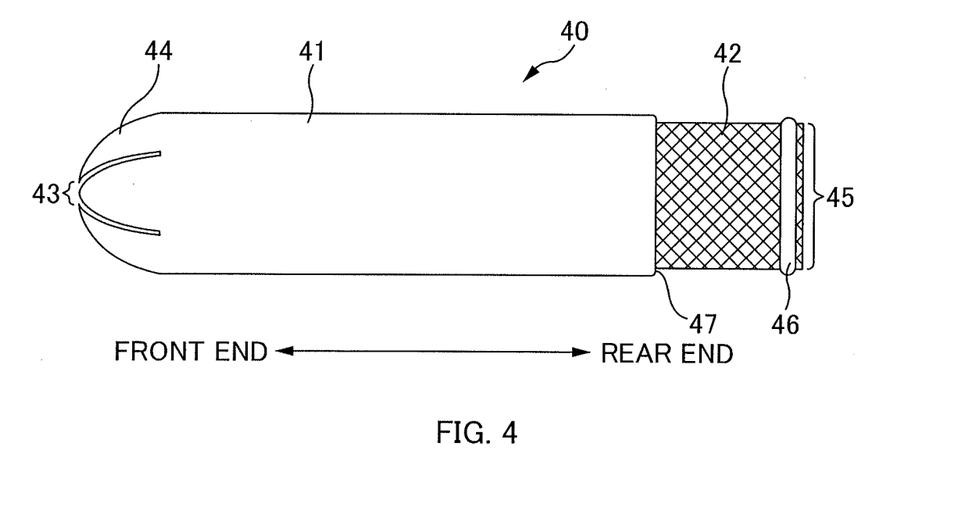
FIG. 4 is an external view of an outer tube 40.
Figure 5:
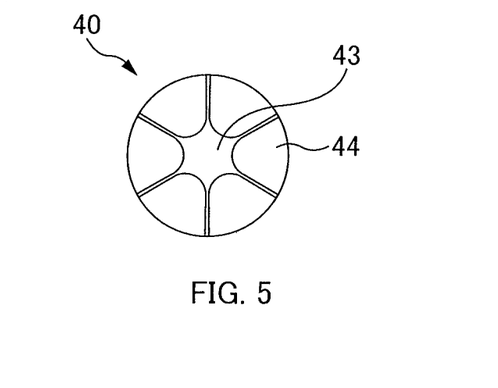
FIG. 5 is a view of the outer tube 40 shown in FIG. 4 from its front end.
Figure 6:
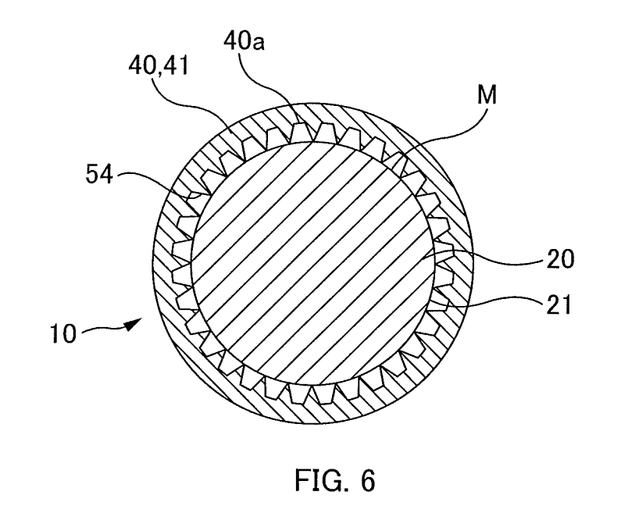
FIG. 6 is a cross-sectional view taken along A-A of FIG. 1 or 2.
Figure 7:
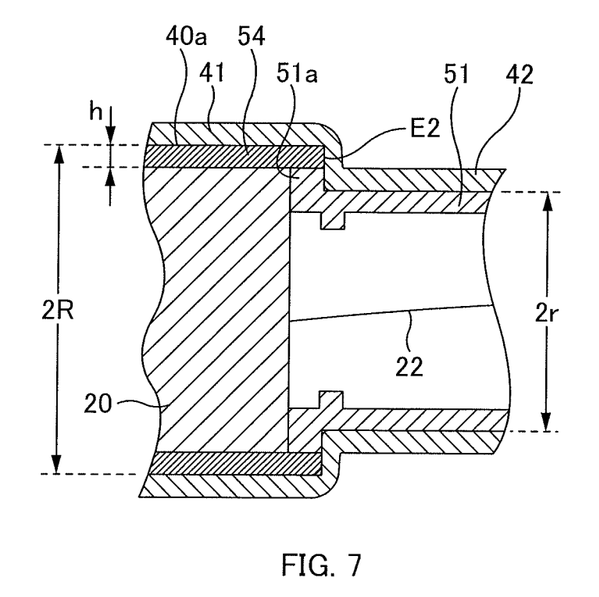
FIG. 7 is a magnified view of FIG. 2.

FIGS. 1 and 2 are cross-sectional views showing components of the tampon 10. FIG. 1 shows the tampon 10 with its inner tube 50 shortened, and FIG. 2 shows the tampon 10 with its inner tube 50 elongated. FIG. 3 is an external view of a tampon body 20. FIG. 4 is an external view of an outer tube 40. FIG. 5 is a view of the outer tube 40 shown in FIG. 4 from its front end. FIG. 6 is a cross-sectional view taken along A-A of FIG. 1 or 2. FIG. 7 is a magnified view of FIG. 2. In the following description, an end inserted into the vaginal cavity in a longitudinal direction of the tampon 10 is referred to as a front end and the opposite end is referred to as a rear end.

As shown in FIGS. 1 and 2, the tampon 10 of the present embodiment includes the tampon body 20 as an example of the absorbent body, and an applicator 30 having the outer tube 40 as an example of housing cylinder and the inner tube 50 as an example of a pushing member.

The tampon body 20 is a thing to fill the vaginal cavity and absorb liquid such as menstrual blood. This tampon body 20 is formed by covering an absorbent main body (wool-like body) made of rayon fiber, with a cover made of polyester spunbond nonwoven fabric. The tampon body 20 is shaped substantially like a bullet.

Further, an agent M adhering on an outer surface 21 of the tampon body 20. This agent M is a light brown colorant (a colored substance), and is a mixture of a pine bark extract (flavangenol (R) manufactured by Toyo Shinyaku Co., Ltd.) and a polyethylene glycol, the pine bark extract being as an example of an active pharmaceutical ingredient that is administered to inside of the vaginal cavity and performs antioxidant activity, anti-inflammatory activity, antibiotic activity, antiviral activity, antiallergic activity, deodorization, vasodilation, inhibitory action on lipid peroxidation etc, and the polyethylene glycol being as an example of a water-soluble carrier that carries the pine bark extract.

More specifically, the agent M according to the present embodiment includes, as water-soluble carrier (polyethylene glycol), two water-soluble carrier whose melting points (in other words, freezing point) are different from each other. In other words, the agent M includes: a polyethylene glycol with a molecular weight of 1540 (hereinafter referred to as a first polyethylene glycol) as an example of a first water-soluble carrier, and a polyethylene glycol with a molecular weight of 1000 (hereinafter referred to as a second polyethylene glycol) as an example of a second water-soluble carrier. The melting point (freezing point) of the first polyethylene glycol is approximately 45° C., higher than body temperature (37° C.).

On the other hand, the melting point (freezing point) of the second polyethylene glycol is approximately 37° C., which is lower than the melting point of the first polyethylene glycol and is lower than or equal to body temperature. As mentioned above, the agent M is a mixture of the pine bark extract, the first polyethylene glycol, and the second polyethylene glycol.

In the present embodiment, the mixture ratio of the pine bark extract, the first polyethylene glycol, and the second polyethylene glycol is 1:3:1 (that is, the pine bark extract has 20 weight percent, the first polyethylene glycol 60 weight percent, and the second polyethylene glycol 20 weight percent). That is, the first polyethylene glycol is a main ingredient of the agent M.

Further, the tampon body 20 according to the present embodiment, as shown in FIG. 3, has a pattern on the outer surface 21. In other words, the tampon body 20 includes on its outer surface 21 the applied portions 23 to which the agent M is applied and non-applied portions 25 to which the agent M is not applied. Also, the pattern is formed on the outer surface 21 by the applied portions 23 and non-applied portions 25 (that is, by the difference in color between the applied portions 23 and non-applied portions 25). The pattern according to the present embodiment is one that is formed by arranging alternately regularly the applied portions 23 and non-applied portions 25. Specifically, the pattern, as shown in FIG. 3, is one that is composed of rings (4 mm in width) lined up in the longitudinal direction of the tampon body 20.

Onto the tampon body 20 according to the present embodiment, a withdrawal string 22 as an example of a string is stitched. This withdrawal string 22 is a cotton string. The withdrawal string 22 extends from the rear end of the tampon body 20, and is held by a user of the tampon while attempting to remove the tampon body 20 out of the vaginal cavity. Further, as shown in FIGS. 1 and 2, the withdrawal string 22 passes inside the applicator 30 and extends somewhat beyond the rear end of the applicator 30 (the inner tube 50). That is, a part of the withdrawal string 22 exposes outside from the rear end of the applicator 30 (the inner tube 50).

In the present embodiment, while the agent M is applied to the tampon body 20 (the applied portions 23 are included), the agent M is not applied to an exposed portion 22a of the withdrawal string 22 (the applied portions 23 are not included). Further, the withdrawal string 22 does not include any of the applied portions 23 (There is no applied portion 23 on the withdrawal string 22).

The applicator 30 is an assisting tool in order to facilitate insertion of the tampon body 20 into the vaginal cavity. The applicator 30 includes the outer tube 40 and the inner tube 50, as shown in FIGS. 1 and 2.

The outer tube 40 is for housing the tampon body 20. The outer tube 40 is a cylinder that is injection-molded from thermoplastic resin (in the present embodiment, polyethylene resin), and has suitable flexibility. The outer tube 40 has a transparency that allows the tampon body 20 housed in the outer tube to be seen from outside (in other words, the pattern formed on the tampon body 20) (for example, haze value of 90% or less; in the present embodiment, 47%). The outer tube 40 may or may not be colored; in the present embodiment, an entire surface of the outer tube 40 is colored light pink.

Further, the outer tube 40 includes: a radially-large portion 41 positioned on the front end side (in other words, the one end side in the longitudinal direction of the outer tube 40), and a radially-small portion 42 that has an internal diameter smaller than that of the radially-large portion 41 and is positioned on the rear end side, opposite the front end side (in other words, the other end side in the longitudinal direction of the outer tube 40) (the radially-large portion 41 is also larger than the radially-small portion 42 in external diameter). The front end section of the outer tube 40 is larger than the rear end thereof in external diameter (internal diameter). Thereby, an annular shoulder 47 is formed between the radially-large portion 41 and radially-small portion 42.

The radially-large portion 41 is a portion of the outer tube 40 and has a function mainly to house the tampon body 20 inside thereof. Indeed, in the tampon 10 according to the present embodiment, the tampon body 20 is housed in the radially-large portion 41 only of the radially-large portion 41 and radially-small portion 42 (therefore, in the longitudinal direction of the outer tube 40, the length of the radially-large portion 41 is larger than that of the tampon body 20). The radially-large portion 41 is a portion that is inserted into the vaginal cavity with housing the tampon body 20 therein when the tampon 10 is used.

Further, the radially-large portion 41 (the outer tube 40) includes an opening (hereinafter referred to as a front-end opening 43) on its front end, and also includes a plurality of petal portions 44 surrounding the front-end opening 43 (in the present embodiment, 6). Each of the plurality of petal portions 44 is bent in the form of an arc radially inwardly of the outer tube 40, as shown in FIG. 4. Therefore, when inserting the outer tube 40 into the vaginal cavity, the front end section of the outer tube 40 is substantially hemisphere in shape as shown in FIGS. 1 and 2, and the front-end opening 43 is substantially closed as shown in FIG. 5. When the tampon body 20 is expelled from the front-end opening 43 by the inner tube 50 described below, the front-end opening 43 opens.

The radially-small portion 42 is a section that provides a space in which of the outer tube 40 the following inner tube 50 mainly moves (However, of course, the inner tube 50 moves not only inside the radially-small portion 42 but also inside the radially-large portion 41). The radially-small portion 42 is a portion that is held by a user when the tampon 10 is used.

Further, the radially-small portion 42 (the outer tube 40) includes an opening (hereinafter referred to as a rear-end opening 45) on the rear end as shown in FIG. 4, and also includes an annular rib 46 that is formed slightly closer to the front end than the rear-end opening 45 is.

As shown in FIGS. 1, 2, 6, and 7, the outer tube 40 includes ribs (hereinafter referred to as a longitudinal ribs 54) on an inner surface 40a thereof (of the outer tube 40) along the longitudinal direction of the outer tube 40. The outer tube 40 according to the present embodiment includes the longitudinal ribs 54 in at least an area that is closer to the front end from a center C in the longitudinal direction of the outer tube 40 (see FIG. 1). Also, in the present embodiment, the outer tube 40 includes the longitudinal ribs 54, on only the radially-large portion 41 of the radially-large portion 41 and the radially-small portion 42.

As shown in FIG. 6, 32 of the longitudinal direction ribs 54 are arranged such that the ribs are equally spaced along the inner circumferential direction of the inner surface 40a. In other words, the outer tube 40 (radially-large portion 41) has three or more longitudinal direction ribs 54 that is arranged such that the ribs 54 are equally spaced along the inner circumferential direction of the inner surface 40a. In the present embodiment, the longitudinal direction ribs 54 that are adjacent to each other are not in contact with each other (do not abut and touch each other).

Each of the longitudinal direction ribs 54 is formed straight from the front end of the radially-large portion 41 to the rear end thereof, as shown in FIGS. 1 and 2. More specifically, the longitudinal direction ribs 54 according to the present embodiment are disposed of the radially-large portion 41 up to an rearmost end E2 thereof, but do not reach an foremost end of the radially-large portion 41. In other words, the petal portions 44 do not have the longitudinal rib 54, and the ribs 54 are disposed of the radially-large portion up to an foremost end E1 thereof except for the petal portions.

Further, as shown in FIG. 6, the longitudinal rib 54 according to the present embodiment is a rib extending radially of the radially-large portion 41, and the width of the rib narrows as it gets closer radially to the center. As shown in FIG. 7, the height h of the longitudinal rib 54 extending radially of the radially-large portion 41 is smaller than the difference of the internal diameters of the radially-large portion 41 and radially-small portion 42 (internal diameter of radially-large portion 41 R−internal diameter of radially-small portion r=R−r) (h<R−r). In other words, the internal diameter R−h of the radially-large portion 41 considering the longitudinal ribs 54 (hereinafter referred to as, for convenience, a rib-considered internal diameter) is larger than the internal diameter r of the radially-small portion (r<R−h).

The tampon body 20 has an external diameter substantially same as rib-considered internal diameter, and the tampon body 20 is housed in the radially-large portion 41 of the outer tube 40, with being in contact only with the longitudinal rib 54 of the inner surface 40a and the longitudinal rib 54, as shown in FIG. 6. In other words, the outer surface 21 of the tampon body 20 is not in contact with the inner surface 40a, and is in contact only with a radially-extending front end section of the longitudinal ribs 54.

The inner tube 50 is for expelling the tampon body 20 from the front-end opening 43 outside the outer tube 40 by moving in the outer tube 40. This inner tube 50 is inserted into the outer tube 40, and is positioned closer to the rear end in the outer tube 40 than the tampon body 20 is. The inner tube 50 moves along the longitudinal direction of the outer tube 40 and pushes the tampon body 20 towards the front-end opening 43 from the rear. Thereby, the tampon body 20 pushes aside each of the plurality of petal portions 44 radially outwardly of the outer tube 40 (in other words, opens the front-end opening 43) and is expelled from the outer tube 40. As mentioned above, the inner tube 50 has a function to expel the tampon body 20 out of the outer tube 40 by moving the outer tube 40.

Further, the inner tube 50 according to the present embodiment has a retractable configuration in order to make the tampon 10 compact in size. Specifically, as shown in FIG. 1, when the inner tube 50 is shortened, the inner tube 50 is shorter in length than the outer tube 40 so that the length of the tampon 10 is suitable for carrying. On the other hand, as shown in FIG. 2, when the inner tube 50 is elongated, the length of the inner tube 50 is sufficient to expel the tampon body 20 outside the outer tube 40. As mentioned above, in order to make the inner tube 50 retractable, in the present embodiment, the inner tube 50 has a dual structure. Specifically, as shown in FIGS. 1 and 2, the inner tube 50 of the present embodiment includes a first inner tube 51, and a second inner tube 52 that is slidably inserted into the first inner tube 51.

The first inner tube 51 is a cylinder that is injection-molded from plastic. The first inner tube 51 has an external diameter that is slightly smaller than the internal diameter of the radially-small portion 42 of the outer tube 40. Also, the first inner tube 51 is slidably inserted into the radially-small portion 42, as shown in FIG. 1. On the outer circumferential face of the front end section of the first inner tube 51, an annular sword-guard portion 51a is formed. This sword-guard portion 51a has an external diameter that is slightly smaller than the rib-considered internal diameter of the radially-large portion 41 of the outer tube 40. Also, the sword-guard portion 51a is stopped by connecting it to an inner wall of the shoulder 47 so that the sword-guard portion 51a prevents the inner tube 50 from falling off the rear-end opening 45 of the outer tube 40. When the inner tube 50 expels the tampon body 20 out of the outer tube 40, the inner tube 50 moves such that the outer circumferential face of the sword-guard portion 51a comes into contact with the longitudinal ribs 54 of the radially-large portion 41. Further, at the rear end section of an inner circumferential face of the first inner tube 51, an annular projection 51b extending radially inwardly of the first inner tube 51 are formed, as shown in FIGS. 1 and 2.

The second inner tube 52 is a cylinder that is injection-molded from thermoplastic resin. This second inner tube 52 has an external diameter slightly smaller than the internal diameter of the first inner tube 51. The second inner tube 52 is inserted into the first inner tube 51 as shown in FIG. 1 when the inner tube 50 is shortened. The second inner tube 52 is connected to the rear end section of the first inner tube 51 at the front end section of the second inner tube 52 as shown in FIG. 2 when the inner tube 50 is elongated. On the outer circumferential face of the front end section of the second inner tube 52, are formed an arc-shaped sword-guard portion 52a and a projection section 52b that is located closer to the rear end than the sword-guard portion 52a is. The height of the projection section 52b is lower as it gets close to the rear end, as shown in FIG. 2. The space between the sword-guard portion 52a and projection section 52b of the second inner tube 52 is slightly larger than the thickness of the annular projection 51b of the first inner tube 51.

When the second inner tube 52 is pulled towards the rear end, the annular projection 51b of the first inner tube 51 is positioned between the sword-guard portion 52a and projection section 52b of the second inner tube 52. At this state, as shown in FIG. 2, the annular projection 51b is stopped by connecting to the sword-guard portion 52a and projection section 52b, and the first inner tube 51 connects to the second inner tube 52.

Further, as shown in FIGS. 1 and 2, a flared portion 52c is formed on rear end section of the second inner tube 52. The external diameter of the flared portion 52c is desirably at least larger than the internal diameter of the first inner tube 51 and larger than or equal to the internal diameter of the radially-small portion 42 of the outer tube 40.

Manufacturing Method For Tampon 10

Figure 8:
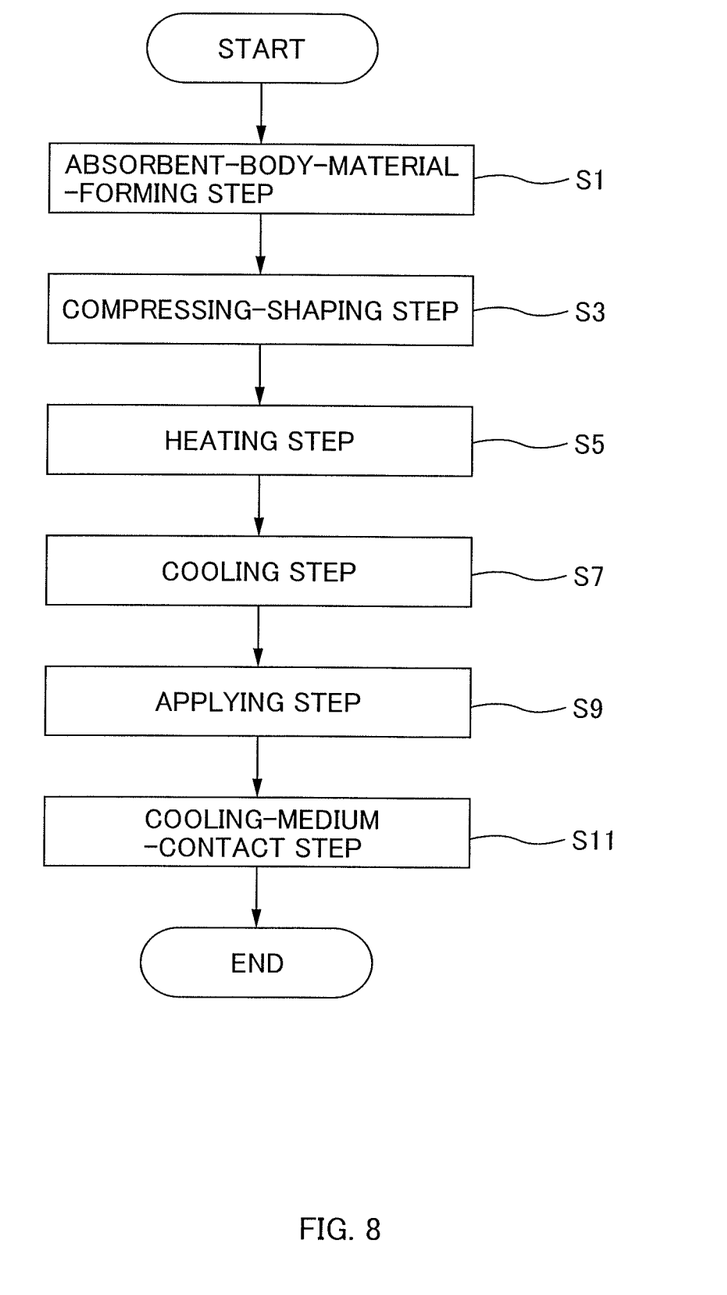
FIG. 8 is a flowchart showing the production flow of the tampon body 20.
Figure 9A:
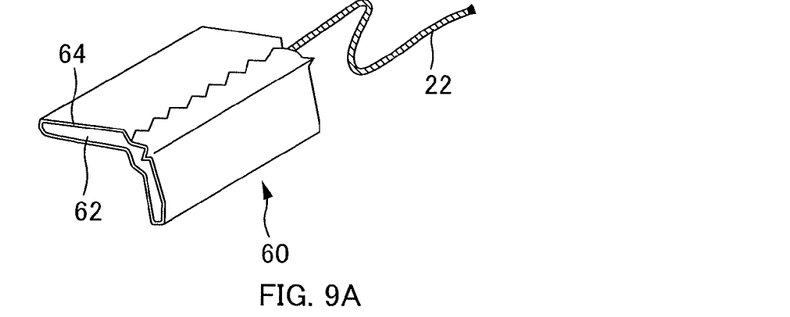
FIGS. 9A to 9D are schematic diagrams showing transition of the tampon body 20 to a finished product.
Figure 9B:
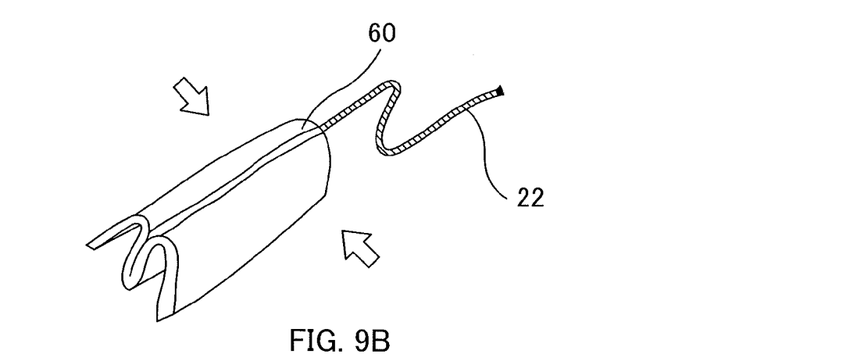
Figure 9C:
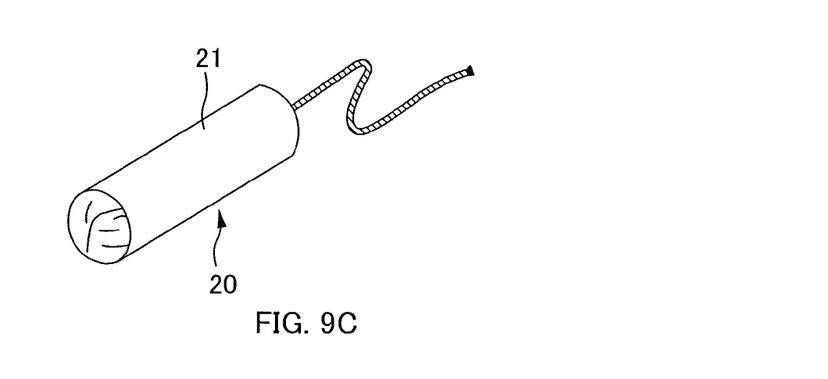
Figure 9D:
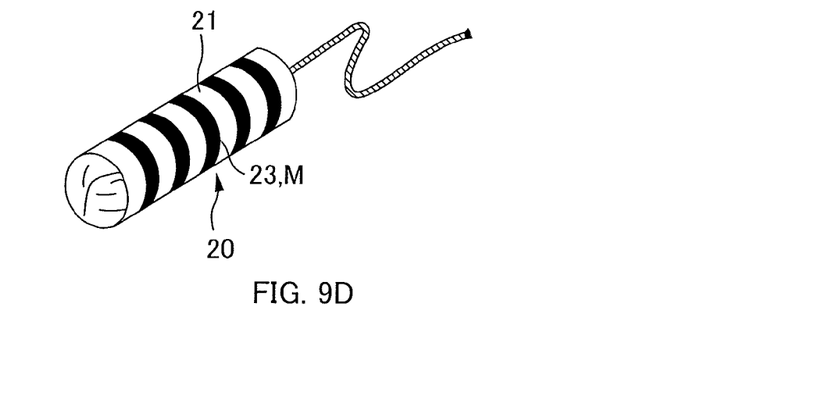
Figure 10:
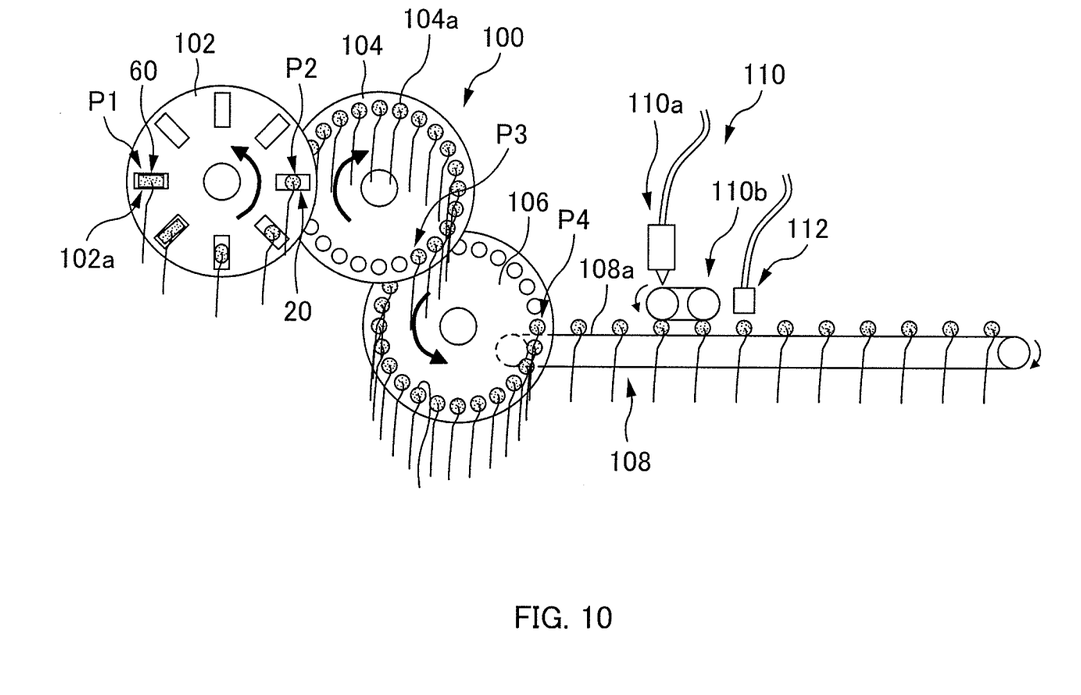
FIG. 10 is a schematic diagram showing a section of the manufacturing apparatus 100 for the tampon 10, which manufactures the tampon body 20.
Figure 11:
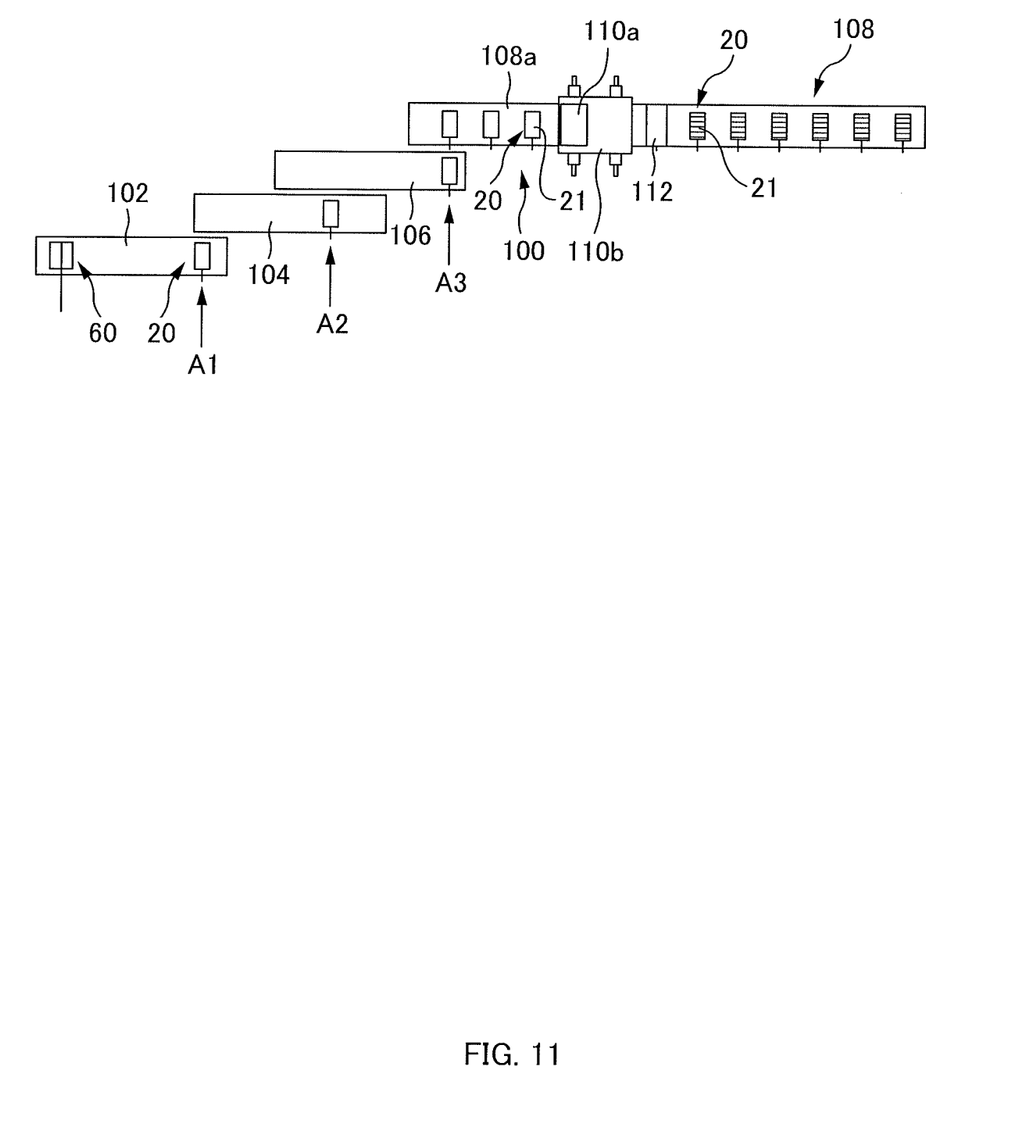
FIG. 11 is a schematic diagram of the manufacturing apparatus 100 shown in FIG. 10 viewed from above.

Next, a manufacturing method for manufacturing the foregoing tampon 10 will be described with reference to FIGS. 8 to 11. FIG. 8 is a flowchart showing the production flow of the tampon body 20. FIGS. 9A to 9D are schematic diagrams showing the transition of the tampon body 20 to a finished product. FIG. 10 is a schematic diagram showing a section of the manufacturing apparatus 100 for the tampon 10, which manufactures the tampon body 20. FIG. 11 is a schematic diagram of the manufacturing apparatus 100 shown in FIG. 10 viewed from above.

The manufacturing process of the tampon 10 is divided into: a process in which the components of the tampon 10 (that is, the tampon body 20, the outer tube 40, the first inner tube 51, and the second inner tube 52) are manufactured, and a process in which these components are assembled. This section will describe the process in which the tampon body 20 (more precisely, the tampon body 20 having the withdrawal string 22) is manufactured.

The production flow of FIG. 8 starts with an absorbent-body-material-forming step (step S1). In this step, firstly, the absorbent main body 62 (wool-like body) is covered with a cover 64 (wrapped with the cover 64). Then, the absorbent main body 62 covered with the cover 64 is cut into a predetermined shape and size. Thereby, an absorbent-body material 60 is formed (that is, the base material of the tampon body 20). In this step, the absorbent-body material 60 undergoes a process in which the withdrawal string 22 is stitched to the absorbent-body material 60 (FIG. 9A shows a state of the absorbent-body material 60 after the step is finished).

Next, the tampon body 20 is obtained by compressing and shaping the absorbent-body material 60 (compression-shaping step of step S3).

FIGS. 10 and 11 shows a compressing-shaping drum 102 as an example of a compressing-shaping unit; the compressing-shaping drum 102 has a function to compress and shape the absorbent-body material 60 (also, the tampon body 20 is obtained thereby). Indeed, the compressing-shaping drum 102 is a drum-shaped rotatable unit, and includes a plurality of holding sections 102a (in the present embodiment, 8) positioned radially. The absorbent-body material 60 is inserted successively into the holding section 102a at a first position P1 (FIG. 10), and the inserted absorbent-body material 60 rotates and moves to a second position P2 (FIG. 10) in conjunction with rotation of the compressing-shaping drum 102. Then, While rotating and moving, the absorbent-body material 60 is compressed from the both side thereof in the holding section 102a (FIG. 9B shows a state of the absorbent-body material 60 being compressed).

Next, by heating the tampon body 20 that is obtained by compressing and shaping the absorbent-body material 60 with the compressing-shaping drum 102, the shape of the tampon body 20 is fixed (heating step of step S5).

FIGS. 10 and 11 shows a heating drum 104 as an example of a heating unit; the heating drum 104 has a function to heat the tampon body 20 that is obtained by compressing and shaping the absorbent-body material 60 with the compressing-shaping drum 102 (further, thereby the shape of the tampon body 20 is fixed). Indeed, the heating drum 104 is a drum-shaped rotatable unit whose temperature is controlled at 110 degree, for example (a temperature between 100 and 180 degree is preferable). The drum 104 includes many of holding sections 104a radially positioned. The tampon body 20 is transferred successively at a second position P2 (FIG. 10) from the holding section 102a of the compressing-shaping drum 102 to the holding section 104a of the heating drum 104, by pushing of a pusher (not shown) (the direction in which the pusher pushes the body is shown with an arrow A1 in FIG. 11). Then, the tampon body 20 that is transferred to the holding section 104a rotates and moves to the third position P3 (FIG. 10) in conjunction with rotation of the heating drum 104. While rotating and moving, the tampon body 20 is heated in the holding section 104a and the shape of the tampon body 20 is fixed. The holding section 104a is a hole having a shape corresponding to the shape of the tampon body 20 (the tampon body 20 fits in the hole). Also, the heat of the heating drum 104 is effectively conducted to the tampon body 20. Further, at the same time when transferring the tampon body 20 from the compressing-shaping drum 102 to the heating drum 104, the tampon body 20 undergoes a process in which the front end is formed in the shape of a bullet. FIG. 9C shows a state of the tampon body 20 after the heating step is finished.

Next, the tampon body 20 whose shape is fixed by the heating drum 104 is cooled (cooling step of step S7).

FIGS. 10 and 11 shows a cooling drum 106 as an example of a cooling unit; the cooling drum 106 has a function to cool the tampon body 20 whose shape is fixed by the heating drum 104. Indeed, the cooling drum 106 is a drum-shaped rotatable unit whose temperature is controlled at 25° C. for example, and includes many of holding sections 106a positioned radially. The tampon body 20 is transferred successively at a third position P3 (FIG. 10) from the holding section 104a of the heating drum 104 to the holding section 106a of the cooling drum 106 by pushing of a pusher (not shown) (the direction in which the pusher pushes the body is shown with an arrow A2 in FIG. 11). Then, the tampon body 20 that is transferred to the holding section 106a rotates and moves to a fourth position P4 (FIG. 10) in conjunction with rotation of the cooling drum 106. While rotating and moving, the tampon body 20 is cooled in the holding section 106a. In similar to the holding section 104a, the holding section 106a is a hole having a shape corresponding to the tampon body 20 (the tampon body 20 fits in the hole), and is configured such that the tampon body 20 is cooled effectively by the cooling drum 106.

The tampon body 20 that has rotated and moved to the fourth position P4 (FIG. 10) is transferred successively at the fourth position P4 from the holding section 106a of the cooling drum 106 to a conveyor unit 108 (specifically, a conveyor belt 108a disposed of the conveyor unit 108) by pushing of a pusher (not shown) (the direction in which the pusher pushes the body is shown with an arrow A3 in FIG. 11). The conveyor belt 108a is an endless conveyor belt for the tampon body; the conveyor belt 108a holds the tampon body 20 such that the longitudinal direction of the tampon body 20 is aligned in the width direction of the conveyor belt 108a. The conveyor belt 108a conveys the tampon body 20 by rotating and moving. The temperature of the conveyor belt 108a is controlled, for example, at 25° C., the conveyor belt 108a also has a function as a cooling unit that cools the tampon body 20. Indeed, the tampon body 20 whose shape is fixed by the heating drum 104 is cooled by the cooling unit, first in the cooling drum 106 and second in the conveyor belt 108a.

Next, melted agent M is applied to the outer surface 21 of the tampon body 20 (applying step of step S9).

FIGS. 10 and 11 shows an applying unit 110, which has a function to apply melted agent M onto the outer surface 21 of the tampon body 20. The applying unit 110 includes a supplying unit 110a and a transferring belt 110b.

The supplying unit 110a is for supplying the melted agent M to the transferring belt 110b. In the present embodiment, the supplying unit 110a melts the agent M and applies the melted agent M to the transferring belt 110b.

The transferring belt 110b is for transferring and applying the melted agent M onto the outer surface 21 while the belt being in contact with the outer surface 21 of the tampon body 20. In the present embodiment, the transferring belt 110b is an endless conveyor belt for an agent, which conveys the agent M by rotating and moving with holding the agent M applied by the supplying unit 110a. Then the conveyed agent M reaches a contact position at which the transferring belt 110b comes into contact with the outer surface 21 of the tampon body 20 being conveyed by the conveyor belt 108a, and the agent M is transferred and applied to the outer surface 21.

As shown in FIG. 10, when the agent M is applied to the outer surface 21, the tampon body 20 is being sandwiched between the transferring belt 110b and the conveyor belt 108a. In the present embodiment, the speeds in the direction from left to right in FIG. 10 (hereinafter referred to as merely a left-to-right direction) are controlled such that the speed of the transferring belt 110b is greater than that of the conveyor belt 108a. Therefore, while the tampon body 20 is sandwiched between the transferring belt 110b and the conveyor belt 108a, the tampon body 20 rotates on the conveyor belt 108a and moves in the left-to-right direction. Therefore (because of the rotation), the agent M is applied onto the entire outer surface 21 of the tampon body 20 circumference-wise.

As mentioned above, the tampon body 20 is cooled by the cooling unit whose temperature is controlled at 25° C. first by the cooling drum 106 and second by the conveyor belt 108a. Therefore, the applying unit 110 applies the melted agent M onto the outer surface 21 of the tampon body 20, the outer surface being cooled to approximately 25° C. by the cooling unit. Because, the melting point (freezing point) of the main ingredient of the agent M (that is, the first polyethylene glycol) is approximately 45° C. as mentioned above, the melted agent M freezes rapidly (instantly) when applying the agent M onto the outer surface 21 of the tampon body 20. As mentioned above, in the cooling step of step S7, the cooling unit cools the tampon body 20 whose shape is fixed by the heating drum 104 so that a temperature of its outer surface 21 becomes a temperature lower than or equal to the freezing point of the main ingredient of the agent M. In the applying step of step S9, the applying unit 110 applies the melted agent M onto the outer surface 21 of the tampon body 20, the outer surface 21 having a temperature lower than or equal to the freezing point (that is, cooled to a temperature lower than or equal to the freezing point).

Next, a cooling medium is brought into contact with the agent M applied to the outer surface 21, the cooling medium being cooled to a temperature lower than or equal to the freezing point of the main ingredient of the agent M (in the present embodiment, approximately 45° C.) (cooling-medium-contact step of step S11).

FIGS. 10 and 11 shows a cool-air-blowing unit 112 as an example of a cooling-medium-contact unit that brings the cooling medium into contact; the cool-air-blowing unit 112 has a function to bring cool air as a cooling medium into contact with the agent M that is applied by the applying unit 110 onto the outer surface 21, the cool air being cooled to a temperature lower than or equal to the freezing point of the main ingredient of the agent M. That is, the cool-air-blowing unit 112 brings the cooling medium into contact with the agent M by blowing cool air onto the agent M, the cool air being cooled to a temperature lower than or equal to 45° C. (in the present embodiment, 25° C.)

Further, as mentioned above, the temperature of the conveyor belt 108a is controlled at 25° C., the conveyor belt 108a is cooled, and the tampon body 20 rotates on the conveyor belt 108a with being sandwiched between the transferring belt 110b and the conveyor belt 108a. As a result, the agent M applied to the outer surface 21 comes instantly into contact with the conveyor belt 108a. Therefore, the conveyor belt 108a has a function as a cooling medium that is cooled to a temperature lower than or equal to the freezing point. In other words, the conveyor unit 108 has a function as a cooling-medium-contact unit that brings the conveyor belt 108a as a cooling medium into contact with the agent M that is applied onto the outer surface 21, the conveyor belt being cooled to a temperature lower than or equal to the freezing point.

As mentioned above, in the present embodiment, the melted agent M is applied onto the outer surface 21 of the tampon body 20 cooled to a temperature lower than or equal to the freezing point. In addition thereto, the agent M applied on the outer surface 21 is brought into contact with the cooling medium cooled to a temperature lower than or equal to the freezing point. Therefore, when the melted agent M is applied to the outer surface 21 of the tampon body 20, the agent M freezes more rapidly. Then, the cooling-medium-contact step is performed, and the manufacturing process of the tampon body 20 is finished. FIG. 9D shows a state of the tampon body 20 after the cooling-medium-contact step is finished.

Effectiveness of Manufacturing Method and Manufacturing Apparatus of Tampon 10 According to the Present Embodiment As mentioned above, the manufacturing method (manufacturing apparatus 100) for tampon 10 according to the present embodiment includes: the compression-shaping step (compressing-shaping drum 102) in which the absorbent-body material 60 is compressed and shaped to obtain the tampon body 20; and the applying step (applying unit 110) in which the melted agent M is applied onto the outer surface 21 of the tampon body 20, the surface 21 having a temperature lower than or equal to the freezing point of the main ingredient of the agent M. Thereby, is achieved the manufacturing method (manufacturing apparatus 100) for the tampon 10 having the agent M that properly takes effect while the tampon being within the vaginal cavity.

Regarding the foregoing, the description will be made comparing the manufacturing method (manufacturing apparatus 100) for the tampon 10 according to the present embodiment (the present example) and two manufacturing methods (manufacturing apparatus) for a tampon according to comparative example.

The first comparative example is a manufacturing method (manufacturing apparatus) in which the agent is applied onto the outer surface of the tampon body prior to compression and shaping the absorbent-body material. For example, in the comparative example, after the agent is applied onto a cover, the absorbent main body is covered with the cover and the absorbent-body material is formed. Thereafter, by compressing and shaping the formed absorbent-body material the tampon body is obtained.

However, such a manufacturing method (manufacturing apparatus) may cause the following problems. Indeed, because the agents are applied onto the absorbent-body material prior to compressing and shaping, the agents may falls off when the absorbent-body material is compressed and shaped. In the case of using such a tampon as the foregoing falling off has happened (in other words, in the case of inserting such a tampon into the vaginal cavity), the agents cannot be transferred to the vaginal mucosa properly because the amount of the agents adhering onto the outer surface decreases. That is, the agent does not properly take effect when a tampon is inserted into vaginal cavity. Also, the falling off may cause a problem that the manufacturing apparatus becomes soiled with the agent.

Further, in order to avoid this problem, a second comparative example is a manufacturing method (manufacturing apparatus) in which the tampon body is dipped into the agents after obtaining the tampon body by compressing and shaping the absorbent-body material. However, in such a manufacturing method (manufacturing apparatus), when the tampon body is dipped into the agents, the agents may be absorbed into the tampon body. In the case of using such a tampon as the foregoing absorption has happened (in other words, in the case of inserting such a tampon into the vaginal cavity), the amount of the agent adhering onto the outer surface decreases. Therefore, the agent cannot be transferred to the vaginal mucosa appropriately. As a result, that is, the agent does not properly take effect when a tampon is inserted into the vaginal cavity. Further, the absorption may cause a problem that the tampon body becomes too large in size.

As mentioned above, in both of manufacturing methods (manufacturing apparatuses) for a tampon according to the comparative examples, the problem that the agents do not properly take effect when the manufactured tampon is inserted into the vaginal cavity may arise.

As opposed thereto, in the manufacturing method (manufacturing apparatus 100) for the tampon 10 according to the present embodiment, after obtaining the tampon body 20 by compressing and shaping the absorbent-body material 60, the agent M is applied to the outer surface 21 of the tampon body 20. Therefore, the falling-off problem will not arise. Also, the melted agent M is applied onto the outer surface 21 of the tampon body 20, the surface 21 having a temperature lower than or equal to the freezing point of the main ingredient of the agent M. Therefore, when the melted agent M is applied onto the outer surface 21 of the tampon body 20, the agent M freezes rapidly (instantly) on the outer surface 21. As a result, the agent M is not absorbed deeper than the outer surface 21 (in other words, inside of the tampon body).

As mentioned above, in the present embodiment, the falling off or absorption is prevented. Therefore, the foregoing problem that the agent M cannot be transferred appropriately to the vaginal mucosa due to decreasing the amount of the agent M adhering onto the outer surface 21 is avoided properly. That is, the manufacturing method (manufacturing apparatus 100) for the tampon 10 having the agent M that properly takes effect while the tampon is inserted in the vaginal cavity is achieved. Also, in the present embodiment, the problem of the manufacturing apparatus soiled with the agent caused by falling off or the problem of the oversized tampon body caused by absorption is avoided properly. Further, in the present embodiment, the falling off or absorption is prevented. This allows a pattern to be formed nicely on the outer surface 21.

Further, the manufacturing method (manufacturing apparatus 100) for tampon 10 according to the present embodiment includes the cooling-medium-contact step (the cool-air-blowing unit 112 and conveyor unit 108 as an example of a cooling-medium-contact unit) in which the cool air and conveyor belt 108a as an example of a cooling medium are brought into contact with the agent M that is applied to the outer surface 21, the cool air and conveyor belt 108a being cooled to a temperature lower than or equal to the freezing point. That is, as mentioned above, the melted agent M is applied onto the outer surface 21 of the tampon body 20, the outer surface 21 having a temperature lower than or equal to the freezing point. In addition thereto, the cooling mediums that are cooled to a temperature lower than or equal to the freezing point come into contact with the agent M applied on the outer surface 21. Therefore, when the melted agent M is applied onto the outer surface 21 of the tampon body 20, the agent M freezes more rapidly on the outer surface 21. Therefore, is achieved the manufacturing method (manufacturing apparatus 100) for the tampon 10 having the agent M that more properly takes effect while the tampon being within the vaginal cavity.

Further, the manufacturing method (manufacturing apparatus 100) for tampon 10 according to the present embodiment includes: the heating step (heating drum 104) in which the tampon body 20 that is obtained by compressing and shaping the absorbent-body material 60 is heated and the shape of the tampon body 20 is fixed; and the cooling step (cooling drum 106 and conveyor belt 108a as an example of a cooling unit) in which the tampon body 20 whose shape is fixed is cooled such that the temperature of the outer surface 21 becomes a temperature lower than or equal to the freezing point. In addition, in the step of applying the agent M (applying unit 110), the melted agent M is applied onto the outer surface 21 of the tampon body 20, the outer surface 21 being cooled to a temperature lower than or equal to the freezing point. That is, in the present embodiment, the outer surface 21 is not left to cool down naturally (that is, the outer surface 21 is not left to cool down naturally to a temperature lower than or equal to the freezing point). In the present embodiment, the cooling step (cooling unit) is employed voluntarily. Thereby the melted agent M is applied onto the outer surface 21 of the tampon body 20, the outer surface 21 being cooled to a temperature lower than or equal to the freezing point. This makes it possible to shorten the manufacturing process.

Further, in the present embodiment, both of the cooling unit and cooling medium are the conveyor belt 108a. That is, cooling the conveyor belt 108a allows the conveyor belt 108a to have functions of the cooling unit and of the cooling medium. Thus, a single member can have a plurality of functions, and the efficient manufacturing apparatus is achieved.

Further, in the present embodiment, the cooling-medium-contact unit is the cool-air-blowing unit 112 that blows the cool air as a cooling medium onto the agent M. That is, as a method for bringing the cooling medium into contact with the agent M applied to the outer surface 21, a method of blowing cool air to agent M is employed. This makes it possible to cool the agent M easily.

Other Embodiments

Above, based on the above embodiments, the manufacturing method and manufacturing apparatus according to the invention is described, but the above embodiments of the invention are for facilitating understanding of the invention, and are not limiting of the invention. The invention can of course be altered and improved without departing from the gist thereof, and equivalents are intended to be embraced therein.

Further, in the foregoing embodiment, the tampon 10 having the applicator 30 is provided as an example of a tampon, but the invention is not limited thereto. A tampon without an applicator can be employed.

Further, in the foregoing embodiment, the pine bark extract is provided as an example of an active pharmaceutical ingredient of the agent M, but the invention is not limited thereto. For example, a plant extract such as red clover, polygonum indigo extract, indirubin or the like can be employed. In addition thereto, Flavangenol® is provided as an example of a pine bark extract, but the invention is not limited thereto. For example, Pycnogenol® which Nihon SiberHegner K.K deals in or Enzogenol® which Valentine Company Limited deals in can be employed.

Further, in the foregoing embodiment, the applying unit 110 applies the agent M only one time, but the invention is not limited thereto. The applying unit 110 can apply the agent M in several operations. In such a case, for example, a plurality of sets of the supplying unit 110a and transferring belt 110b are used and applying of the agent M is done in several operations.

Further, in the foregoing embodiment, the applying unit 110 that has the supplying unit 110a and transferring belt 110b is provided as an example of an applying unit, but the invention is not limited thereto. For example, the applying unit 210 that has a moving unit 212 and a heating-transferring unit 214 to be described below can be employed.

Figure 12:
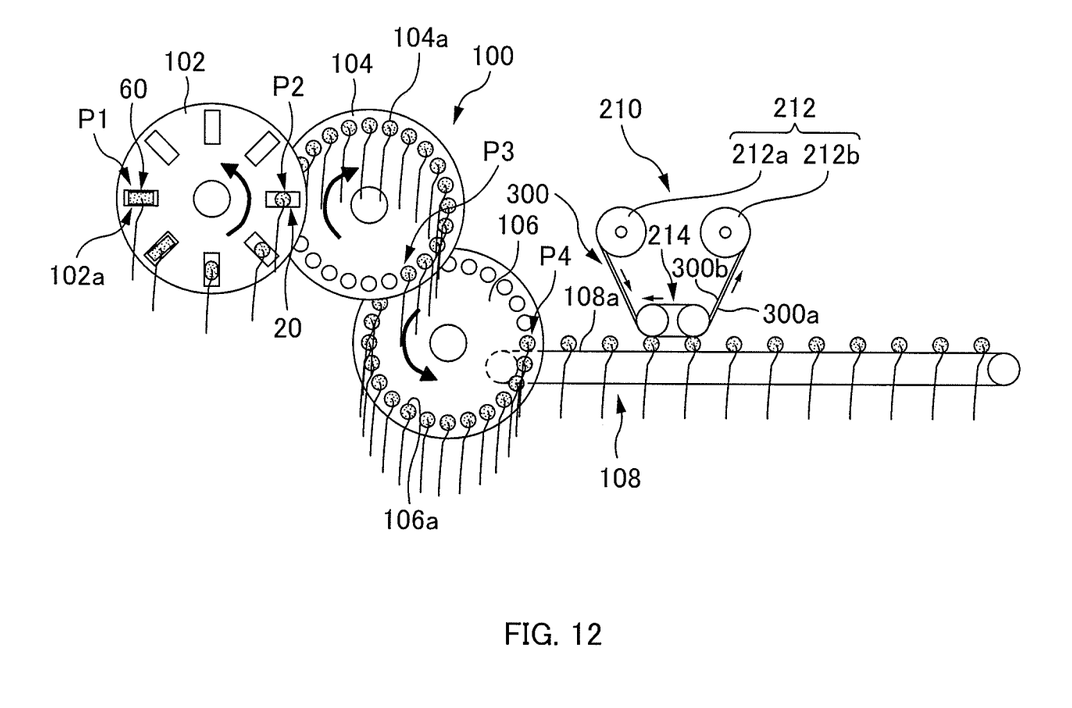
FIG. 12 is a schematic diagram showing a section of the manufacturing apparatus 100 for the tampon 10 according to the other embodiment, which manufactures the tampon body 20.

With reference to FIG. 12, the more description will be made. FIG. 12 corresponds to FIG. 10, and is a schematic diagram showing a section of the manufacturing apparatus 100 for the tampon 10 according to the other embodiment, which manufactures the tampon body 20. FIG. 12 shows an applying unit 210; the applying unit 210 has a function to apply melted agent M onto the outer surface 21 of the tampon body 20, and includes the moving unit 212 and heating-transferring unit 214.

The moving unit 212 is for moving the frozen-agent-adhering sheet 300 that includes the frozen agent M adhering onto a one surface 300a thereof, while the one surface 300a being in contact with the outer surface 21 of the tampon body 20. This moving unit 212 includes two rollers around which the frozen-agent-adhering sheet 300 is wrapped (that is, a sheet-supply roller 212a and a sheet-take-up roller 212b). These two rollers work together (specifically, rotate together) to move the frozen-agent-adhering sheet 300. The frozen-agent-adhering sheet 300 according to the present embodiment is a film that is made of polypropylene or polyester, the film having the agent M that adheres to the one surface 300a thereof in advance. The frozen-agent-adhering sheet 300 is manufactured in a different process from the manufacturing process of the tampon body 20. The frozen-agent-adhering sheet 300 moves with its one surface 300a being pressed against the outer surface 21 of the tampon body 20 by the heating-transferring unit 214 to be described below.

The heating-transferring unit 214 is for melting the frozen agent M and transferring the melted agent M to the outer surface 21 by heating the frozen-agent-adhering sheet 300 with keeping in contact with another surface 300b of the sheet 300. This heating-transferring unit 214 is a heated endless belt. This heating-transferring unit 214 comes into contact with the other surface 300b and rotates and moves with heating the frozen-agent-adhering sheet 300 while pressing the one surface 300a against the outer surface 21 of the tampon body 20. By heating as mentioned above, the frozen agent M that adheres to the one surface 300a of the moving frozen-agent-adhering sheet 300 is melted and is transferred to the outer surface 21 (the agent M is applied onto the outer surface 21).

As shown in FIG. 12, when the agent M is applied onto the outer surface 21, the tampon body 20 is being sandwiched between the frozen-agent-adhering sheet 300 and the conveyor belt 108a. In the present embodiment, the speeds in the direction from left to right in FIG. 12 (hereinafter referred to as merely a left-to-right direction) are controlled such that the speed of the frozen-agent-adhering sheet 300 is greater than that of the conveyor belt 108a. Therefore, with being sandwiched between the frozen-agent-adhering sheet 300 and the conveyor belt 108a, the tampon body 20 rotates on the conveyor belt 108a and moves in the left-to-right direction. Therefore (because of the rotation), the agent M is applied onto the entire outer surface 21 of the tampon body 20 circumference-wise.

As mentioned above, the applying unit may include: the transferring belt 110b that transfers and applies the melted agent M to the outer surface 21 with being in contact with the outer surface 21 of the tampon body 20; and the supplying unit 110a that supplies the transferring belt 110b with the melted agent M. Also, the applying unit may include: a moving unit 212 that moves the frozen-agent-adhering sheet 300 having the frozen agent M that adheres to the one surface 300a thereof, with the one surface 300a being in contact with the outer surface 21 of the tampon body 20; and a heating-transferring unit 214 that melts the frozen agent M and transfers the melted agent M to the outer surface 21 by keeping in contact with the other surface 300b of the frozen-agent-adhering sheet 300 and heating the sheet 300. The former is superior because it is unnecessary to preparing a thing such as a frozen-agent-adhering sheet in advance, which makes the manufacturing process simpler. The latter is superior because the agent M does not melt (freezes) immediately before the agent M is transferred to the outer surface 21, which makes it possible to configure a manufacturing apparatus that is difficult to be soiled with the agent M. Of course, the applying unit is not limited to these two. For example, the applying unit may be a stamp unit or a non-contact ink jet unit.

REFERENCE SIGNS LIST 10 tampon, 20 tampon body (absorbent body), 21 outer surface,
22 withdrawal string, 22a exposed portion, 23 applied portion, 25 non-applied portion,
30 applicator, 40 outer tube, 40a inner surface, 41 radially-large portion,
42 radially-small portion, 43 front-end opening, 44 petal portion, 45 rear-end opening,
46 annular rib, 47 shoulder, 50 inner tube, 51 first inner tube,
51a sword-guard portion, 51b annular projection, 52 second inner tube, 52a sword-guard portion,
52b projection section, 52c flared portion, 54 longitudinal rib,
60 absorbent-body material, 62 absorbent main body, 64 cover,
100 manufacturing apparatus, 102 compressing-shaping drum (compressing-shaping unit),
102a holding section, 104 heating drum (heating unit), 104a holding section,
106 cooling drum (cooling unit), 106a holding section,
108 conveyor unit (cooling-medium-contact unit),
108a conveyor belt (cooling unit, cooling medium),
110 applying unit, 110a supplying unit, 110b transferring belt,
112 cool-air-blowing unit (cooling-medium-contact unit),
210 applying unit, 212 moving unit,
212a sheet-supply roller, 212b sheet-take-up roller,
214 heating-transferring unit, 300 frozen-agent-adhering sheet,
300a one surface, 300b the other surface,
C center, E1 foremost end, E2 rearmost end, M agent

The invention claimed is:

1. A apparatus for manufacturing a tampon having an absorbent body for absorbing liquid, said apparatus comprising:
    a compressing-shaping unit for compressing and shaping an absorbent-body material to obtain the absorbent body;
    a heating unit for heating the absorbent body to fix a shape of the absorbent body;
    a conveyor belt for conveying the absorbent body in a conveying direction and for cooling the absorbent body;
    a transferring belt for transferring and applying a melted agent to an outer surface of the absorbent body while the transferring belt is in contact with the outer surface; and
    a supplying unit for supplying the melted agent to the transferring belt;
    wherein
    the transferring belt and the conveyor belt are configured to sandwich the absorbent body while rotating and moving the absorbent body on the conveyor belt in the conveying direction.

2. The apparatus according to claim 1, wherein the apparatus further comprises
    a cooling-medium-contact unit for bringing a cooling medium into contact with the agent applied by the transferring belt to the outer surface of the absorbent body, the cooling medium being cooled to a temperature lower than or equal to a freezing point of a main ingredient of the agent.

3. The apparatus according to claim 2, wherein
the cooling-medium-contact unit is a cool-air-blowing unit for blowing cool air, as the cooling medium, onto the agent.

4. The apparatus according to claim 3, wherein the cool-air-blowing unit is located downstream of the supplying unit in the conveying direction.

5. The apparatus according to claim 2, wherein the freezing point of the main ingredient is approximately 45° C.

6. The apparatus according to claim 1, further comprising:
a cooling unit for cooling the absorbent body whose shape is fixed by the heating unit such that the outer surface of the absorbent body has a temperature lower than or equal to a freezing point of a main ingredient of the agent,
wherein the transferring belt is configured to apply the melted agent to the cooled outer surface of the absorbent body.

7. The apparatus according to claim 6, further comprising a cooling-medium-contact unit for bringing a cooling medium into contact with the agent applied by the transferring belt to the outer surface, the cooling medium being cooled to a temperature lower than or equal to the freezing point, and the cooling medium includes the conveyor belt.

8. The apparatus according to claim 6, wherein the cooling unit includes the conveyor belt.

9. The apparatus according to claim 1, further comprising:

a moving unit for moving a frozen-agent-adhering sheet having a first surface with the agent in a frozen state in contact with the outer surface of the absorbent body, and a heating-transferring unit for melting the agent in the frozen state and transferring the melted agent to the outer surface, the heating-transferring unit configured to maintain contact with a second surface of the frozen-agent-adhering sheet and to heat the agent in the frozen state on the first surface through the frozen-agent-adhering sheet.

10. The apparatus according to claim 1, wherein a moving speed of the transferring belt is greater than a moving speed of the conveyor belt.

11. The apparatus according to claim 1, wherein the transferring belt is configured to transfer and apply the melted agent onto an entirety of the outer surface of the absorbent body in a circumferential direction of the absorbent body.

12. The apparatus according to claim 1, wherein the transferring belt is configured to contact the outer surface extending in a circumferential direction of the absorbent body.

* * * * *